United States Patent [19]
Ozeretskovskaya et al.

[11] 3,956,369
[45] May 11, 1976

[54] N-β-(2-ACETYL-4-CHLOROPHENOXY)-ETHYL-N,N-DIMETHYL-N-BENZYL-AMMONIUM-P-CHLOROBENZENE SULPHONATE, METHOD FOR PREPARING SAME AND MEDICINAL PREPARATION BASED THEREON

[76] Inventors: Natalia Nikolaevna Ozeretskovskaya, Lomonosovsky prospekt 14, kv. 184; Vladimir Kuzmich Karnaukhov, Zhivopisnaya ulitsa 34/14, kv, 7; Alexandr Markusovich Bronshtein, Glinisty pereulok 12, kv. 17; Vera Fedorovna Gladkikh, ulitsa Ostuzheva 19/6, kv. 18; Marina Nikolaevna Lebedeva, ulitsa Obrucheva, 9, kv. 83; Elvira Vasilievna Sazonova, Festivalnaya ulitsa, 11, kv. 59; Nelli Dmitrievna Lychko, 3 Frunzenskaya ulitsa, 26, kv. 55; Andrei Ivanovich Krotov, Profsojuznaya ulitsa 102, korpus 5, kv. 109; Olga Evgenievna Kuznetsova, Vinnitskaya ulitsa, 5, kv. 12; Alla Fedorovna Bekhli, Rostovskaya Naberezhnaya 3, kv. 32; Maria Borisovna Braude, Festivalnaya ulitsa 7, kv. 18; Ljubov Alexeevna Bolotina, Novokhoroshevskoe shosse, korpus 1, dom 8, kv. 72; Renata Leonidovna Polovinchik, ulitsa Nizhnyaya Maslovka, 14, kv. 67; Boris Alexandrovich Astafiev, Otkrytoe shosse, 6, korpus 7, kv. 44, all of Moscow, U.S.S.R.

[22] Filed: May 18, 1973

[21] Appl. No.: 361,847

[52] U.S. Cl. .................. 260/501.15; 260/567.6 M; 424/329
[51] Int. Cl.² ....................................... C07C 93/14
[58] Field of Search ........................... 260/501.15

[56] References Cited
UNITED STATES PATENTS

| | | | |
|---|---|---|---|
| 1,867,022 | 7/1932 | Mune et al. | 260/501.15 |
| 3,328,464 | 6/1967 | Gundel et al. | 260/501.15 |
| 3,714,256 | 1/1973 | Samour et al. | 260/501.15 |

FOREIGN PATENTS OR APPLICATIONS

| 924,961 | 5/1963 | United Kingdom | 260/501.15 |

OTHER PUBLICATIONS

Chem. Abstracts, 8th Collective Index, Vol. 66–75, p. 20825 (1967–1971); Krotov et al, Chem. Abs., 70, 46407m (1969).
Petkov et al, Chem. Abstract, 75, 40426y (1971).

*Primary Examiner*—James O. Thomas, Jr.
*Assistant Examiner*—Nicky Chan
*Attorney, Agent, or Firm*—Holman & Stern

[57] ABSTRACT

A compound N-β(2-acetyl-4-chlorophenoxy)-ethyl-N,N-dimethyl-N-benzylammonium-p-chlorobenzene sulphonate having the formula:

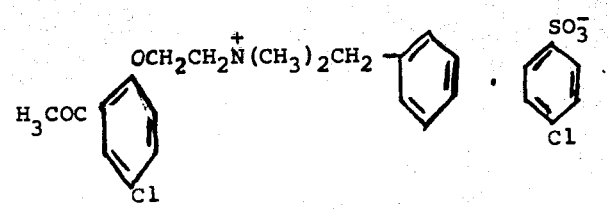

This compound is prepared by reacting 2-hydroxy-5-chloroacetophenone and β-dimethylaminoethyl chloride with heating in a medium of an organic solvent in the presence of an alkali agent, reacting the resulting 2-acetyl-4-chlorophenoxyethyl-dimethylamine with benzyl chloride, and subsequently reacting the resulting N-β-(2-acetyl-4-chlorophenoxy)-ethyl-N,N-dimethyl-N-benylammonium chloride with a sodium salt of p-chlorobenzene sulphonic acid.

This compound exhibits anthelmintic activity for *Trichocephalus muris* in albine mice.

1 Claim, No Drawings

N-β-(2-ACETYL-4-CHLOROPHENOXY)-ETHYL-N,N-DIMETHYL-N-BENZYL-AMMONIUM-P-CHLOROBENZENE SULPHONATE, METHOD FOR PREPARING SAME AND MEDICINAL PREPARATION BASED THEREON

The present invention is concerned with a novel substance, viz. N-β-(2-acetyl-4-chlorophenoxy)-ethyl-N,N-dimethyl-N-benzylammonium-p-chlorobenzene sulphonate, a method for preparing same and a medicinal preparation based thereon.

Said substance, according to the invention, has the following formula:

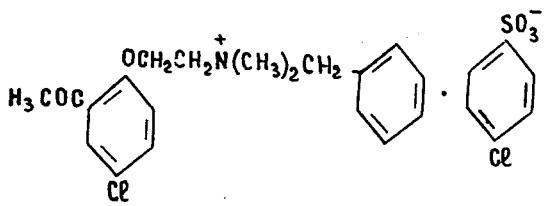

The proposed new compound is a white crystalline powder, bitter to taste, sparingly soluble in water, soluble with heating in alcohol, acetone, insoluble in ether. The melting point, 172°–172.5°C.

N-β-(2-acetyl-4-chlorophenoxy)-ethyl-N,N-dimethyl-N benzylammonium-p-clorobenzene sulphonate has antitricho-cephalous activity and is used in medicine as a preparation for treating trichocephalosis.

According to the invention, the method for preparing N-β-(2-acetyl-4-chlorophenoxy)-ethyl-N,N-dimethyl-N-benzylammonium p-chlorobenzene sulphonate consists in that 2-hydroxy-5-chloroacetophenone is reacted with β-dimethylaminoethyl chloride or with its hydrochloride, which are taken with a 80 percent excess, in the presence of sodium hydroxide in a medium of benzene or toluene at a temperature of 80°–100°C with the formation of 2-acetyl-4-chlorophenoxydimethylamine, which is reacted with benzyl chloride at a temperature of 80°–90°C with the formation of N-β-(2-acetyl-4-chlorophenoxy)-ethyl-N,N-dimethyl-N-benzylammonium chloride, whose aqueous solution is reacted with an aqueoues solution of p-chlorobenzenesulphonic acid sodium salt at a temperature not above 20°C with the formation and isolation of the end product.

In order to intensify the process for preparing N-β-(2-acetyl-4-chlorophenoxy)-ethyl-N,N-dimethyl-N-benzyl ammonium chloride, it is recommendable to react 2acetyl-4-chlorophenoxyethyldimethylamine with benzyl chloride in a medium of acetone or benzene at a temperature of the solution boiling point.

N-β-(2-acetyl-4-chlorophenoxy)-ethyl-N,N-dimethyl-N-benzylammonium p-chlorobenzene sulphonate is the active principle of a medicinal preparation used to treat trichocephalosis. It is administered in the powder form per se, or in the tablet form in combination with a pharmaceutical excipient (0.25–0.5 g of the active principle per tablet weighing 0.29–0.58 g). When given in the powder form, the preparation is recommended to be enclosed in capsules; when, in tablets, it should be protected with a coating soluble in the intestinal secretion only.

The new preparation is given the name "Bemosat".

Known in the prior art are other methods to treat trichocephalosis, for example, with naphthamon (alcopar), oxygen, methylene blue, diathermia, which produce but insignificant antitrichocephalotic effect.

The therapeutic efficacy of a 5-day course of oxygen therapy is only 15–25 percent. The efficacy of naphthamon in treating trichocephalosis is only 25–40 percent, and the incidence of side effects is as great as 50–60%.

Diphezyl has been recently offered for treating trichocephalosis, its efficacy being 60–80 percent.

The proposed new preparation for treating trichocephalosis, viz., N-β-(2-acetyl-4-chlorophenoxy)-ethyl-N,N-dimethyl-N-benzyl-ammonium p-chlorobenzene sulphonate, has a positive advantage over diphezyl with respect to its efficacy, which is as high as 85–95 per cent, moreover, the proposed preparation is much less toxic and the process for synthesizing it is less complicated.

The antitrichocephalotic activity of "Bemosat" was studied in experiments on albino mice infected by Trichocephalus muris. The studies have shown that the efficacy of the new preparation is 81 percent at a daily dose of 0.5 g per kg body weight in a course of four days, and 100 percent at a daily dose of 1 g/kg for a course of four days.

White rats and mice well tolerate the preparation to 10 g per kg body weight when given in a single dose.

The study of pharmacodynamics of "Bemosat" as compared with that of diphezyl and naphthamon has shown that the toxicity of "Bemosat" with respect to its action on laboratory animals is less marked as compared with diphezyl, and with naphthamon, in particular.

The new preparation "Bemosat" has been tried clinically in trichocephalotic cases.

It was given to 85 patients with trichocephalosis, aged from 7 to 15. Out of the 85 patients, 48 were treated for fresh cases of trichocephalosis, and 37 had been treated earlier for trichocephalosis with naphthamon, diphezyl, dithiazanin (or dilombrin), oxygen, enteroseptol, which proved of no effect. The new preparation "Bemosat" has revealed parasitological and clinical effects in 87.5 percent cases. In 57 patients, which were observed after treatment, both effects were stable. No deviations of the laboratory indices were observed. Electrocardiographic changes were noted in 2 out of 29 aggravated cases. In 30 out of 47 patients treated with "Bemosat" the stools (2–5 times per day) were liquid (as a rule, in the first three days of the therapy). In 5 out of 38 patients, who took the preparation before meals, nausea and vomiting were observed. The preparation is better tolerated when given after meals.

The preparation was given in the powder form in capsules or in tablets coated with compounds soluble in the intestine secretion. The preparation was given in daily doses of 5 g for adults and children over 12; children of 9–11 were given 4 g a day, 7–8, 3 g., and under seven 2–2.5g. The preparation was given three times a day, 30–40 minutes after meals. The course of the therapy was five days.

The proposed preparation is non-toxic and has high efficacy in treating trichocephalosis. There are no contraindications for using the preparation.

The preparation is used as powder (in capsules) or in tablets. It is kept in jars with ground-in stoppers under NTP conditions.

The proposed method for preparing N-β-(2-acetyl-4-chlorophenoxy)-ehtyl-N,N-dimethyl-N-benzylammonium p-chlorobenzene sulphonate consists in the interaction between 2-acetyl-4-chlorophenoxyethyldimethylamine and benzyl chloride at 80–90°C, as a result of which N-β-(2-acetyl-4-chlorophenoxy)-ethyl-N,N-dimethyl-N-benzylammonium chloride is prepared, which is dissolved in water after cooling the reaction mixture, and the aqueous solution is shaken with benzene, the aqueous layer is separated, carbon is added to it, the mixture is passed through a filter, and the filtrate is added with stirring to an aqueous solution of a sodium salt of p-chlorobenzene sulphonic acid at 20°C. The precipitate of N-β-(2-acetyl-4-chlorphenoxy)-ethyl-N,N-dimethyl-N-benzylammonium p-chlorobenzene sulphonate is separated on a filter, washed with water, dried at 80°C and crystallized from ethyl alcohol (1:5) with carbon additive.

N-β-(2-acetyl-4-chlorophenoxy)-ethyl-N,N-dimethyl-N-benzylammonium chloride can be prepared also by the interaction between equimolecular quantities of 2-acetyl-4-chlorophenoxyethyldimethylamine and benzyl chloride in the presence of acetone or benzene at a temperature of the solution boiling point, with stirring. The thus-prepared chloride is separated on a filter, washed with the solvent, dried at 80°C, dissolved in water, and the aqueous solution of the chloride is added with stirring to an aqueous solution of a sodium salt of p-chlorobenzene sulphonic acid, with subsequent processing the precipitated N-β-(2-acetyl-4-chlorophenoxy)-ethyl-N,N-dimethyl-N-benzylammonium p-chlorobenzenesulphonate, as has been described above.

The intermediate product 2acetyl-4-chlorophenoxyethyldimethylamine is prepared by condensation of 2-hydroxy-5-chloroacetophenone chloride or its hydrochloride in the presence of sodium hydroxide in a medium of benzene or toluene, at a temperature of 80°–82°C, in the case of benzene, or at a temperature of 90°–100°C, in the case of toluene, for 9–10 hours. As the reaction mixture is cooled, water is added to it, the organic layer is separated, and the aqueous layer is extracted two times with the solvent. The organic solutions are washed with a solution of sodium hydroxide and water, and the solvent is removed by distillation. The residue, which is 2-acetyl-4-chlorophenoxyethyldimethylamine, is distilled in vacuum or used without distillation.

For a better understanding of the invention it will be illustrated by the following examples of its practical embodiment.

EXAMPLE 1.

Preparing 2-acetyl-4-chlorophenoxyethyldimethylamine a. 156 g (1.07 mole) of β-dimethylaminoethylhydrochloride are dissolved in 120 ml of water, mixed with 400 ml of benzene and then gradually, with stirring, a solution of 43.5 g (1.08 mole) of sodium hydroxide in 90 ml of water in is added. The benzene layer is separated, the aqueous layer is extracted two times with 50-ml portions of benzene. The benzene solution of β-dimethylaminoethyl chloride is added to a mixture of 102.3 g (0.6 mole) of 2-hydroxy-5-chloroacetophenone and 24 g (0.6 mole) of sodium hydroxide. The mixture is boiled with stirring for nine hours, the reaction mixture is cooled, 250 ml of water added, and the aqueous layer is separated and extracted two times with 50 ml portions of benzene. The benzene solutions are put together and washed, first with a 5 percent solution of sodium hydroxide (four times by 50-ml portions) and then with water. Benzene is then removed by distillation, and the crystalline residue (m.p. 38°–39°C) is distilled in vacuum. The boiling point is 151°–155°C/l mm. the melting point is 43°–44°C., the yield is 103.9 g, (72 percent, as calculated with reference to the starting 2-hydroxy-5-chloroacetophenone. The product is a pale-yellow powder, its alcoholic solution does not colour an aqueous solution of $FeCl_3$ (unlike 2-hydroxy-5-chloroacetophenone).

Found, in percent: Cl, 15.06, 15.13; N, 5.75, 5.78; $C_{12}H_{16}ClNO_2$ Calculated, in percent: Cl, 14.7; N, 5.78.

2-acetyl-4-chlorophenoxyethyldimethylamine in a solution of ethyl alcohol (1:1) with alcoholic solution of HCl, forms the hydrochloride, the melting point of which is 177.5°–178°C.

Found, in percent: Cl (as chloride ion), 12.58; 12.8. $C_{12}H_{16}ClNO_2 \cdot HCl$ Calculated, in percent: chloride ions, 12.75.

b. 54 g (0.37 mole) of βdimethylaminoethyl chloride are dissolved in 40 ml of water, mixed with 100 ml of toluene, and a solution of 15 g (0.37 mole) of sodium hydroxide in 30 ml of water are added with stirring. The toluene layer is separated, the aqueous layer is extracted two times wth 4 50-ml portions of toluene. The toluene extracts are joined and added to a mixture of 42.6 g (0.25 mole) of 2-hydroxy-5-chloroacetophenone and 10 g of (0.25 mole) of sodium hydroxide. The mixture is heated for nine hours at 90°–100°C, with stirring, and 100 ml of water are added. The aqueous layer is separated and extracted two times with 30 ml portions of toluene. The toluene extracts are joined, washed with a 5 percent solution of sodium hydroxide and then with water. Toluene is removed by distillation and the residue is then distilled in vacuum.

The yield of 2-acetyl-4-chlorophenoxyethyldimethylamine (b.p. 151°–156°C/l mm) is 42.3 g (70 percent) as calculated for the starting 2-hydroxy-5-chloroacetophenone. The product is a pale-yellow powder, melting at 43°–44°C.

Preparing N-β-(2-acetyl-4-chlorophenoxy)-ethyl-N,N-dimethyl-N-benzylammonium chloride.

a. A solution of 120.9 g (0.5 mole) of 2-acetyl-4-chlorophenoxyethyldimethylamine and 69.5 g (0.55 mole) of benzyl chloride in 600 ml of acetone is heated with boiling and stirring for 8 hours. The reaction mixture is then cooled, the precipitate is separated by filtration, washed with acetone and dried at 80°C. The yield is 130.8 g (71%). The product is a white powder, melting at 161°–162.5°C. and readily soluble in water.

Found, in percent: chloride ion, 9.47; 9.56. $C_{19}H_{23}Cl_2NO_2$. Calculated, in percent: chloride ion, 9.65.

b. A solution of 58 g (0.24 mole) of 2-acetyl-4-chlorophenoxyethyldimethylamine and 30.4 g (0.24 mole) of benzyl chloride in 20 ml of benzene is heated with boiling and stirring for 12 hours. The reaction mixture is then cooled, the precipiate is separated by filtration and washed with benzene. The yield of N-β-(2-acetyl-4-chlorophenoxy)-ethyl-N,N-dimethyl-N-benzylammonium chloride is 68 g (76%); the melting point is 160°–161°C.

Preparing p-chlorobenzene sulphonate of N-β-(2-acetyl-4-chlorophenoxy)-ethyl-N,N-dimethyl-N-benzylammonium.

A solution of 130.8 g (0.355 mole) of N-β-(2-acetyl-4-chlorophenoxy)-ethyl-N,N-dimethyl-N-benzylammonium chloride in 650 ml of water is added at a slow rate to a solution of a sodium salt of p-chlorobenzene sulphonic acid (104 g or 0.445 mole) in 470 ml of water at 20°C. The mixture is stirred for 30 minutes and allowed to stand overnight. The precipitate is separated on a filter, washed with water till no chlorine is detected in the washings, and dried at 80°C. The yield of p-chlorobenzene sulphonate of N-β-(2-acetyl-4-chlorophenoxy)-ethyl-N,N-dimethyl-N-benzylamine is 169 g (91 percent). This is a white powder with a creamy tint, melting at 168°–168.5°C. After crystallization from 680 ml of ethyl alcohol with an additive of 5 g of carbon, the product is a white powder melting at 172°–172.5°C; the yield is 146 g (88.5%).

Found, in percent: C, 57.37; 57.29; H, 5.41; 5.40; N, 2.62; 2.95; Cl, 13.52; 13.85; S, 6.22; 6.32; $C_{25}H_{27}Cl_2NO_5S$. Calculated, in percent: C, 57.25; H, 5.19; N, 2.68; Cl, 13.5; S, 6.12.

EXAMPLE 2

Preparing 2-acetyl-4-chlorophenoxyethyldimethylamine a. A mixture of 34.1 g (0.2 mole) of 2-hydroxy-5-chloroacetophenone, 52 g (0.36 mole) of β-dimethylaminoethyl hydrochloride, 22.4 g (0.56 mole) of sodium hydroxide and 200 ml of toluene is heated at 90–100°C for 9 hours with stirring. 100 ml of water are added to the reaction mixture, the toluene layer is separated and the aqueous layer is extracted two times with 50-ml portions of toluene. The toluene solutions are joined and washed with a 5 percent solution of sodium hydroxide and water. Toluene is then removed by distillation and the residue (37.4 g, or 77.6%) is distilled in vacuum. The yield is 32 g (66 percent), the boiling point of 2-acetyl-4-chlorophenoxyethyldimethylamine is 150°–156°C/1mm the melting point, 43°–44°C.

b. a mixture of 34.1 g (0.2 mole) of 2-hydroxy-5-chloroacetophenone, 52 g (0.36 mole) of β-dimethylaminoethyhydrochloride, 22.4 g (0.56 mole) of sodium hydroxide and 200 ml of benzene is heated at 80°–82°C for nine hours with stirring. Then 100 ml of water are added to the reaction mixture, the benzene layer is separated, and the aqueoues layer is extracted two times with 50-ml portions of benzene. The benzene extracts are joined and washed with a 5 percent solution of sodium hydroxide and water. Benzene is then removed by distillation and the residue (40 g or 83 percent) is distilled in vacuum. The resultant product is 31.2 g (64.4 percent) of 2-acetyl-4-chlorophenoxyethyldimethylamine having the boiling point at 160°C/2–3 mm. This is a pale yellow powder melting at 43°–44°C.

Preparing p-chlorobenzene sulphonate of N-β-(2-acetyl-4-chlorophenoxy)-ethyl-N,N-dimethyl-N-benzylammonium.

A mixture of 24.2 g (0.1 mole) of 2-acetyl-4-chlorophenoxyethyldimethylamine and 13.9 g (0.11 mole) of benzyl chloride is heated with stirring on a boiling bath for two hours. The mixture is cooled and 200 ml of water are added to the solidified mass. The solution is shaken with 30 ml of benzene, the aqueous layer is separated, 1 g of carbon is added, and the mixture is passed through a filter. The filterate is added to a solution of a sodium salt of p-chlorobenzene sulphonic acid (30 g or 0.13 mole in 150 ml of water) at 20°C. The precipitate is separated on a filter, washed with water until no chlorine in detected in the washings, and dried at 80°C. The yield is 40 g (76.2 percent); the melting point is 165°–169°C. After crystallization from 200 ml of ethyl alcohol (with an additive of 2 g of carbon), 34 g (64.8%) of p-chlorobenzene sulphonate of N-β-(2-acetyl-4-chlorophenoxy)-ethyl-N,N-dimethyl-N-benzylammonium are obtained. The melting points is 172°–172.5°C.

What is claimed is:

1. N-β-(2-acetyl-4-chlorophenoxy)-ethyl-N,N-dimethyl-N-benzylammonium p-chlorobenzene sulphonate having the formula

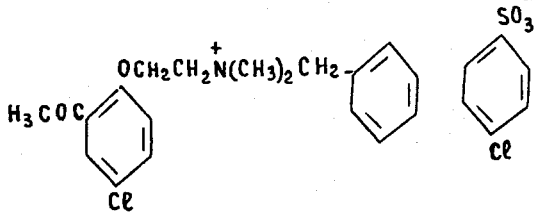

* * * * *